United States Patent [19]

Kummer et al.

[11] 4,105,765
[45] Aug. 8, 1978

[54] 2-(N-(1,3-DIAMINO-ISOPROPYL)-AMINO)-4-PHENYL-2-IMIDAZOLINES AND SALTS THEREOF

[75] Inventors: Werner Kummer; Helmut Stähle; Herbert Köppe, all of Ingelheim am Rhein; Walter Haarmann, Biberach an der Riss; Richard Reichl, Ingelheim am Rhein, all of Fed. Rep. of Germany

[73] Assignee: Boehringer Ingelheim GmbH, Ingelheim am Rhein, Fed. Rep. of Germany

[21] Appl. No.: 837,692

[22] Filed: Sep. 29, 1977

Related U.S. Application Data

[63] Continuation-in-part of Ser. No. 692,325, Jun. 3, 1976, Pat. No. 4,058,616.

[30] Foreign Application Priority Data

Jun. 10, 1975 [DE] Fed. Rep. of Germany ....... 2525725

[51] Int. Cl.² .............. C07D 413/14; A61K 31/415; A61K 31/495; A61K 31/535
[52] U.S. Cl. .............. 424/248.56; 424/250; 544/82; 544/357
[58] Field of Search .............. 260/268 H; 544/82; 424/248.56, 250

[56] References Cited

U.S. PATENT DOCUMENTS 4,058,616  11/1977  Kummer et al. ............. 260/268 H

*Primary Examiner*—Jose Tovar
*Attorney, Agent, or Firm*—Hammond & Littell

[57] ABSTRACT

A compound of the formula

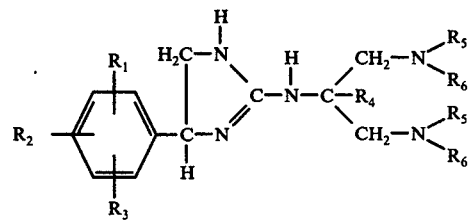

wherein
$R_1$ is chlorine, bromine, fluorine or methyl;
$R_2$ and $R_3$, which may be identical to or different from each other, are each hydrogen, chlorine or methyl;
$R_4$ is hydrogen, methyl or ethyl; and
$R_5$ and $R_6$, together with each other and the nitrogen atom to which they are attached, are morpholino, piperazino or N-methylpiperazino;

and non-toxic, pharmaceutically acceptable acid addition salts thereof; the compounds as well as the salts are useful as antithrombotics.

6 Claims, No Drawings

2-(N-(1,3-DIAMINO-ISOPROPYL)-AMINO)-4-PHENYL-2-IMIDAZOLINES AND SALTS THEREOF

This is a continuation-in-part of copending application Ser. No. 692,325, filed June 3, 1976, now U.S. Pat. No. 4,058,616, granted Nov. 11, 1977.

This invention relates to novel 2-[1,3-diamino-isopropyl)-amino]-4-phenyl-2-imidazolines and acid addition salts thereof, as well as to a method of preparing these compounds.

More particularly, the present invention relates to a novel class of compounds represented by the formula

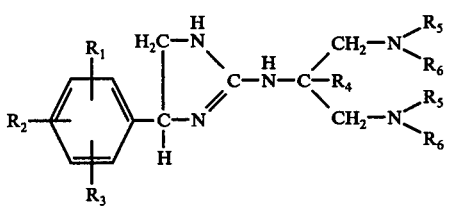

wherein $R_1$ is chlorine, bromine, fluorine or methyl; $R_2$ and $R_3$, which may be identical to or different from each other, are each hydrogen, chlorine or methyl;

$R_4$ is hydrogen, methyl or ethyl; and $R_5$ and $R_6$, together with each other and the nitrogen atom to which they are attached, are morpholino, piperazino or N-methyl-piperazino;

and non-toxic, pharmaceutically acceptable acid addition salts thereof.

The compounds embraced by formula I are cyclic guanidines which occur in tautomeric forms; they contain an asymmetric carbon atom and therefore exist as racemic mixtures or optically active antipodes.

The compounds of this invention may be prepared by reacting a 4-phenyl-2-imidazoline of the formula

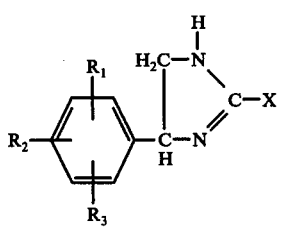

wherein $R_1$, $R_2$ and $R_3$ have the same meanings as in formula I, and

X is chlorine, bromine, iodine, alkoxy of 1 to 4 carbon atoms or alkyl (of 1 to 4 carbon atoms) - mercapto, with a triaminoalkane of the formula

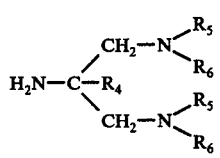

wherein $R_4$, $R_5$ and $R_6$ have the same meanings as in formula I. The reaction is preferably carried out by heating a simple mixture of the reactants, but it will also proceed in the presence of a solvent medium, such as dimethylsulfoxide, dimethylformamide, an alcohol or an ether.

The starting compounds of the formula II wherein X is halogen are accessible by reacting a phenyl-substituted ethylenediamine of the formula

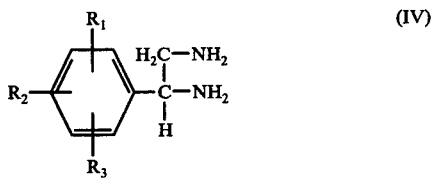

wherein $R_1$, $R_2$ and $R_3$ have the same meanings as in formula I, with a bifunctional carbonic acid derivative, such as phosgene, a chlorocarbonic acid ester or an orthocarbonic acid ester, to form the corresponding ethyleneurea, followed by halogenation of the latter with an inorganic acid halide, such as phosphorus-oxychloride or -oxybromide, or phosphorus-pentachloride, -pentabromide or -pentaiodide, or with a thionyl halide.

The starting compounds of the formula II wherein X is alkylmercapto may, for example, be obtained by reacting a phenyl-substituted ethylenediamine of the formula IV with carbon disulfide to form the corresponding phenyl-substituted ethylenethiourea, followed by alkylation of the latter with an alkyl halide or an inorganic acid alkyl ester, such as dimethyl sulfate.

A phenyl-substituted ethylenediamine of the formula IV, in turn, may be obtained by reacting a correspondingly substituted benzaldehyde with ammonium cyanide, and hydrogenating the α-cyano-benzylamine formed thereby.

The compounds embraced by formula I are organic bases and therefore form acid addition salts with inorganic or organic acids. Examples of non-toxic, pharmaceutically acceptable acid addition salts are those formed with hydrochloric acid, hydrobromic acid, hydriodic acid, hydrofluoric acid, sulfuric acid, phosphoric acid, nitric acid, acetic acid, propionic acid, butyric acid, valeric acid, caproic acid, capric acid, oxalic acid, malonic acid, succinic acid, glutaric acid, maleic acid, fumaric acid, lactic acid, tartaric acid, citric acid, malic acid, gluconic acid, benzoic acid, p-hydroxybenzoic acid, phthalic acid, cinnamic acid, salicyclic acid, ascorbic acid, 8-chlorotheophylline, methanesulfonic acid or the like.

The following examples illustrate the present invention and will enable others skilled in the art to understand it more completely. It should be understood, however, that the invention is not limited solely to the particular examples given below.

EXAMPLE 1

2-[N-(1,3-Bis-diethylamino-isopropyl)-amino]-4-(2,6-dichloro-phenyl)-2-imidazoline monohydrochloride 6.5 gm (0.022 mol) of 4-(2,6-dichloro-phenyl)-2-methylmercapto-2-imidazoline hydrochloride and 10.65 gm (0.053 mol) of N-(1,3-bis-diethylamino-isopropyl)-amine were admixed by stirring, and the mixture was slowly heated to 100° C, whereupon a significant amount of methylmercaptan was given off and the temperature of the mixture spontaneously rose to 130° C. The reaction mixture was maintained at this temperature for 30 minutes, was then cooled to 40° C and at that temperature admixed with 15 ml of acetone. A crystalline substance separated out, which was collected and washed with a mixture of acetone and ether (1:1), yielding 4.2 gm of the hydrochloride of the formula

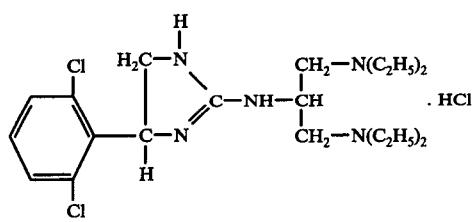

After recrystallization from water, the salt had a melting point of 192° C.

EXAMPLE 2

Using a procedure analogous to that described in Example 1, 2-[N-(1,3-dimorpholino-isopropyl)-amino]-4-(2,6-dichloro-phenyl)-2-imidazoline trioxalate, m.p. 115° C, of the formula

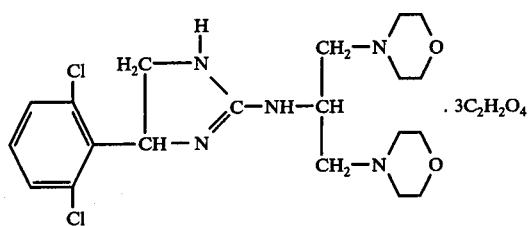

was prepared from 4-(2,6-dichloro-phenyl)-2-methyl-mercapto-2-imidazoline hydrochloride and N-(1,3-dimorpholino-isopropyl)-amine.

EXAMPLE 3

Using a procedure analogous to that described in Example 1, 2-[N-(1,3-bis-(N'-methyl-piperazino)-isopropyl)-amino]-4-(2,6-dichloro-phenyl)-2-imidazoline pentaoxalate, m.p. 69° C (decomp.), of the formula

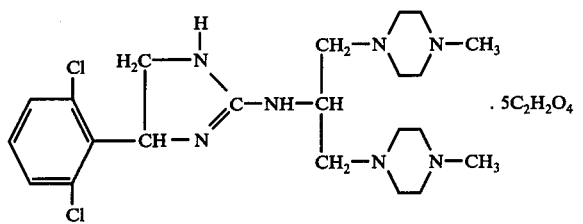

was prepared from 4-(2,6-dichloro-phenyl)-2-methyl-mercapto-2-imidazoline hydrochloride and N-[1,3-bis-(N'methyl-piperazino)-isopropyl]-amine.

EXAMPLE 4

Using a procedure analogous to that described in Example 1, 2-[N-(1,3-dimorpholino-isopropyl)-amino]-4-(2,4,6-trimethyl-phenyl)-2-imidazoline trioxalate, m.p. 185° C, was prepared from 4-(2,4,6-trimethyl-phenyl)-2-methylmercapto-2-imidazoline hydrochloride and N-(1,3-dimorpholino-isopropyl)-amine.

The compounds of the present invention, that is, those embraced by formula I above, have useful pharmacodynamic properties. More particularly, they inhibit blood platelet aggregation and enhance the blood flow in warm-blooded animals, such as dogs, guinea pigs and cats. Therefore, the compounds are useful for propylactic and therapeutic treatment of thromboembolisms and inadequate blood flow in the peripheral and cerebral blood vessels.

The platelet aggregation inhibiting activity of the compounds of this invention was ascertained by the method of Born, which showed that the effective concentrations are $10^{-5}$ mol/liter and more.

For pharmaceutical purposes the compounds of the present invention are administered to warm-blooded animals enterally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective oral dosage unit of the compounds according to the present invention is from 0.00083 to 1.3 mgm/kg body weight, preferably 0.0016 to 0.33 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 5

Tablets

The tablet composition is compounded from the following ingredients:

| | |
|---|---|
| 2-[N-(1,3-Dimorpholino-isopropyl)-amino]-4-(2,6-dichloro-phenyl)-2-imidazoline hydrochloride | 30 parts |
| Corn starch | 160 parts |
| Secondary calcium phosphate | 250 parts |
| Magnesium stearate | 5 parts |
| Total | 445 parts |

Preparation

The individual ingredients are intimately admixed with each other, the mixture is granulated in conventional manner, and the granulate is compressed into 445 mgm-tablets. Each tablet contains 30 mgm of the imidazoline compound and is an oral dosage unit composition with effective antithrombotic action.

EXAMPLE 6

Gelatin capsules

The capsule filler composition is compounded from the following ingredients:

| | |
|---|---|
| 2-[N-1,3-Dimorpholino-isopropyl)-amino]-4-(2,4-dichloro-phenyl)-2-imidazoline trioxalate | 25 parts |
| Corn starch | 175 parts |
| Total | 200 parts |

Preparation

The ingredients are intimately admixed with each other, and 200 mgm-portions of the mixture are filled into gelatin capsules of suitable size. Each capsule contains 25 mgm of the imidazoline compound and is an oral dosage unit composition with effective antithrombotic action.

EXAMPLE 7

Hypodermic solution

The solution is compounded from the following ingredients:

| | |
|---|---|
| 2-[N-(1,3-Dimorpholino-isopropyl)-amino]-4-(2,6-dimethyl-phenyl)-2-imidazoline hydrochloride | 1.5 parts |
| Sodium salt of EDTA | 0.2 parts |
| Distilled water    q.s.ad | 100.0 parts |

Preparation

The imidazoline compound of the EDTA salt are dissolved in a sufficient amount of distilled water, the solution is diluted with additional distilled water to the indicated amount, the resulting solution is filtered until free from suspended particles, and the filtrate is filled into 2 ml-ampules under aseptic conditions. The filled ampules are then sterilized and sealed. Each ampule contains 20 mgm of the imidazoline compound, and its contents are an injectable dosage unit composition with effective antithrombotic action.

Analogous results are obtained when any one of the other compounds embraced by formula I or a non-toxic, pharmacologically acceptable acid addition salt thereof is substituted for the particular imidazoline compound in Examples 5 through 7. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the formula

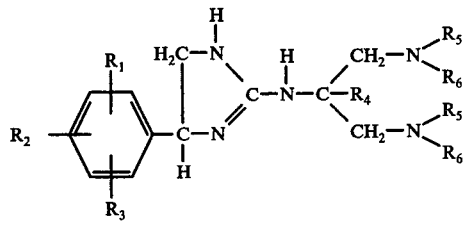

wherein
$R_1$ is chlorine, bromine, fluorine or methyl;
$R_2$ and $R_3$ are each hydrogen, chlorine or methyl;
$R_4$ is hydrogen, methyl or ethyl; and
$R_5$ and $R_6$, together with each other and the nitrogen atom to which they are attached, are morpholino, piperazino or N-methyl-piperazino;
or a non-toxic, pharmaceutically acceptable acid addition salt thereof.

2. A compound of claim 1, which is 2-[N-(1,3-dimorpholino-isopropyl)-amino]-4-(2,6-dichlorophenyl)-2-imidazoline or a non-toxic, pharmaceutically acceptable acid addition salt thereof.

3. A compound of claim 1, which is 2-[N-(1,3-dimorpholino-isopropyl)-amino]-4-(2,4,6-trimethyl-phenyl)-2-imidazoline or a non-toxic, pharmaceutically acceptable acid addition salt thereof.

4. A compound of claim 1, which is 2-[N(1,3-bis-(N'-methyl-piperazino)-isopropyl)-amino]-4-(2,6-dimethyl-phenyl)-2-imidazoline or a non-toxic, pharmaceutically acceptable acid addition salt thereof.

5. An antithrombotic pharmaceutical dosage unit composition consisting essentially of an inert pharmaceutical carrier and an effective antithrombotic amount of a compound of claim 1.

6. The method of inhibiting thrombocyte aggregation in a warm-blooded animal in need thereof, which comprises enterally or parenterally administering to said animal an effective antithrombotic amount of a compound of claim 1.

* * * * *